(12) United States Patent
Jenkins

(10) Patent No.: US 12,369,956 B2
(45) Date of Patent: Jul. 29, 2025

(54) PEDICLE SCREW REMOVAL DEVICE

(71) Applicant: John Jenkins, Windermere, FL (US)

(72) Inventor: John Jenkins, Windermere, FL (US)

(73) Assignee: Argos Industries Florida, LLC, Indian Harbour Beach, FL (US)

( * ) Notice: Subject to any disclaimer, the term of this patent is extended or adjusted under 35 U.S.C. 154(b) by 412 days.

(21) Appl. No.: 18/091,608

(22) Filed: Dec. 30, 2022

(65) Prior Publication Data

US 2023/0404635 A1    Dec. 21, 2023

Related U.S. Application Data

(60) Provisional application No. 63/353,127, filed on Jun. 17, 2022.

(51) Int. Cl.
*A61B 17/70* (2006.01)

(52) U.S. Cl.
CPC ................. *A61B 17/7091* (2013.01)

(58) Field of Classification Search
CPC ...... A61B 17/7091; A61B 17/92; B25B 27/18
See application file for complete search history.

(56) References Cited

U.S. PATENT DOCUMENTS 10,792,079 B1 * 10/2020 Hamade ............. A61B 17/7082
2021/0068882 A1 * 3/2021 Ortiz ................... A61B 17/7082

* cited by examiner

*Primary Examiner* — Andrew Yang
(74) *Attorney, Agent, or Firm* — Harvey S. Kauget, Esq.; Burr & Forman LLP

(57) ABSTRACT

A pedicle screw removal device is provided. The pedicle screw removal device may include a head cap configured to fit over a pedicle screw head, at least one hole in the head cap corresponding to a groove in the pedicle screw head, a removal rod configured to fit through the at least one hole in the head cap and the groove in the pedicle screw head to facilitate rotating the pedicle screw during removal, and a removal handle having a socket, the socket configured to engage the head cap and rotate the head cap to remove the pedicle screw in response to rotation of the removal handle.

14 Claims, 8 Drawing Sheets

PEDICLE SCREW REMOVAL DEVICE

CROSS-REFERENCE TO RELATED APPLICATION

This application claims the benefit of U.S. Provisional Patent Application No. 63/353,127, filed on Jun. 17, 2022, which is incorporated herein by reference in its entirety.

FIELD

The present disclosure relates generally to the field of spine surgery and more particularly to tools designed to remove pedicle screws that have been used in spinal surgeries.

BACKGROUND

Pedicle screws are used in a spinal fusion to add extra support and strength to the fusion while it heals. The pedicle screw, which is sometimes used as an adjunct to spinal fusion surgery, provides a means of gripping a spinal segment. The screws themselves do not fixate the spinal segment, but act as firm anchor points that can then be connected with a rod. Pedicle screws are placed above and below a disc space that is to be fused. A rod is used to connect the screws which prevents movement and allows the bone graft to fuse a segment.

The use of pedicle screws has improved spinal fusion rates. Many surgeons also believe that pedicle screws enhance patient recovery by providing immediate stability for the spine and early mobilization for the patient.

Often times problems develop at levels adjacent to a previously fused segment and new screws need to placed and old screws need to be removed. Thus, there is a need for pedicle screw removal devices that allow for more efficient and safe removal of pedicle screws.

SUMMARY

The present disclosure relates to pedicle screw removal devices for pedicle screws that are used in spine surgery to fuse vertebrae together during a spinal fusion procedure.

According to an aspect of one or more example embodiments, there is provided a pedicle screw removal device that may include a head cap configured to fit over a pedicle screw head, at least one hole in the head cap corresponding to a groove in the pedicle screw head, a removal rod configured to fit through the at least one hole and the groove in the pedicle screw head to facilitate rotating the pedicle screw during removal, and a removal handle configured to engage the head cap and rotate the head cap to remove the pedicle screw in response to rotation of the removal handle.

The head cap may include a body and at least one arm extending substantially perpendicularly from the body. The at least one hole may include a hole in each of the at least one arms, and the hole in each of the at least one arms may be configured to receive the removal rod. The at least one arm may be sized and shaped to engage the removal rod when the removal rod is disposed with the hole in each of the at least one arms, and rotate the pedicle screw in response to rotation of the removal handle.

The head cap may include first and second arms extending substantially perpendicularly from the body. The first arm may include a first hole, and the second arm may include a second hold, the first and second holes for receiving the removal rod. The first and second arms are configured to fit on opposite sides of the pedicle screw head, and are configured to rotate the pedicle screw by rotating the removal rod.

According an aspect of or more example embodiments, there is provided a pedicle screw removal device including a first handle having a first arm with a first hole, a second handle having a second arm with a second hole, and a removal rod configured to pass through the first hole, through a head of a pedicle screw, and through the second hole, and one or more fastening mechanisms configured to couple the first handle and to the second handle.

The pedicle screw removal device may include a t-bar having a cavity configured to fit over the first handle and the second handle. The pedicle screw removal device may also include a first grip portion coupled to the first handle and a second grip portion coupled to the second handle. The first grip portion may extend substantially perpendicularly from the first handle, and the second grip portion may extend substantially perpendicularly from the second handle. The first grip portion and the second grip portion may extend in substantially opposite directions. The t-bar may have a cavity configured to fit over the first grip portion and the second grip portion. The one or more fastening mechanisms may include one or more bolts coupled to the first handle and configured to extend through one or more respective holes in the second handle, and one or more nuts configured to be respectively coupled to the one or more bolts.

According to an aspect of one or more example embodiments, there is provided a pedicle screw removal device that may include a head cap configured to engage a pedicle screw, the head cap including a first vertical portion and a second vertical portion separated from each other to form a cavity therebetween, an integral removal rod coupled to or integrally formed with the first and second vertical portions of the head cap, the integral removal rod configured to fit through a groove in a screw head of the pedicle screw, and a removal handle having a socket configured to engage the head cap and rotate the head cap to remove the pedicle screw in response to rotation of the removal handle. The pedicle screw removal device may include a screw cap insert sized and shaped to fit within the cavity formed between the first and second vertical portions of the head cap. The integral removal rod may be coupled to or integrally formed with end portions of the first and second vertical portions of the head cap.

DETAILED DESCRIPTION OF EXAMPLE EMBODIMENTS

The present disclosure and accompanying figures presents a pedicle screw removal device that assists with removal of pedicle screws. Example embodiments of the pedicle screw removal may increase the safety of removing a pedicle screw by decreasing the risk of breakage of the screw during removal and decreasing the amount of time needed to remove a screw. Various embodiments of the pedicle screw removal device may be adapted for certain types of pedicle screws.

Figure 1:
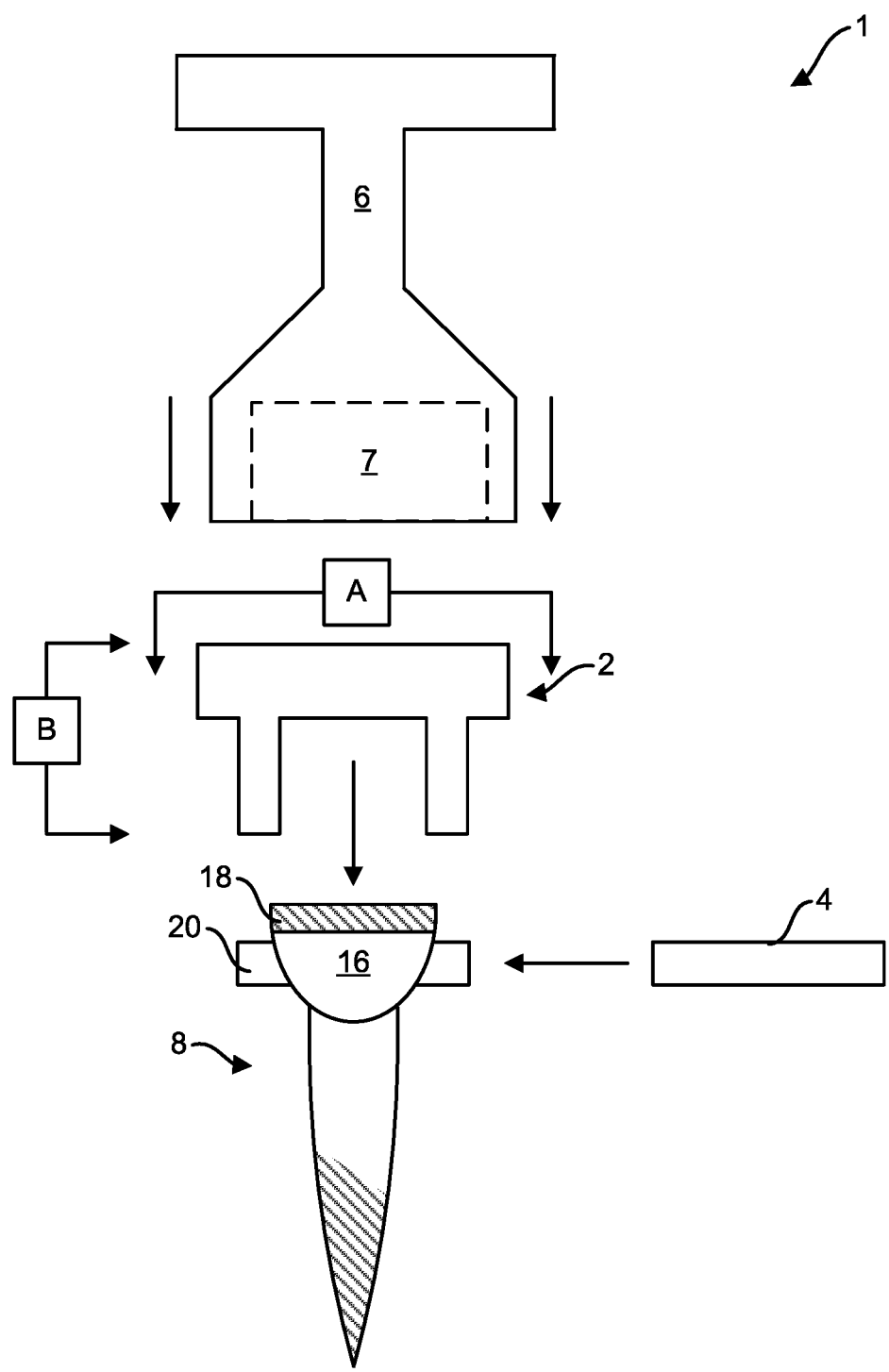
FIG. 1 illustrates a pedicle screw removal device according to an example embodiment.

Referring to FIG. 1, an example embodiment of a pedicle screw removal device is shown. The pedicle screw removal device 1 may include a head cap 2, a removal rod 4, and a removal handle 6. The head cap 2 may be configured to be placed over and secured to a pedicle screw 8 by the removal rod 4. The removal handle 6 may include a socket 7 and the socket 7 may have a cross-section that corresponds to a cross-section of the head cap 2.

Figure 2:
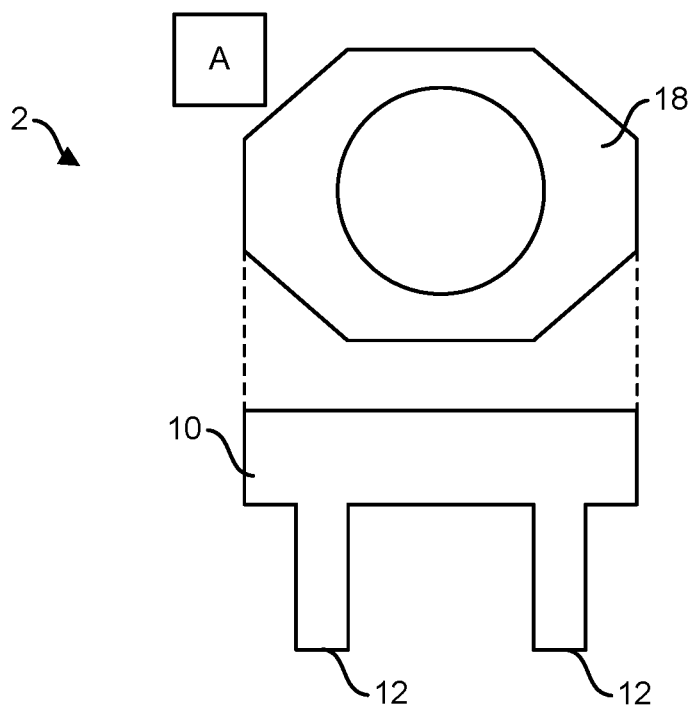
FIG. 2 is a top view of a head cap of a pedicle screw removal device according to an example embodiment.
Figure 3:
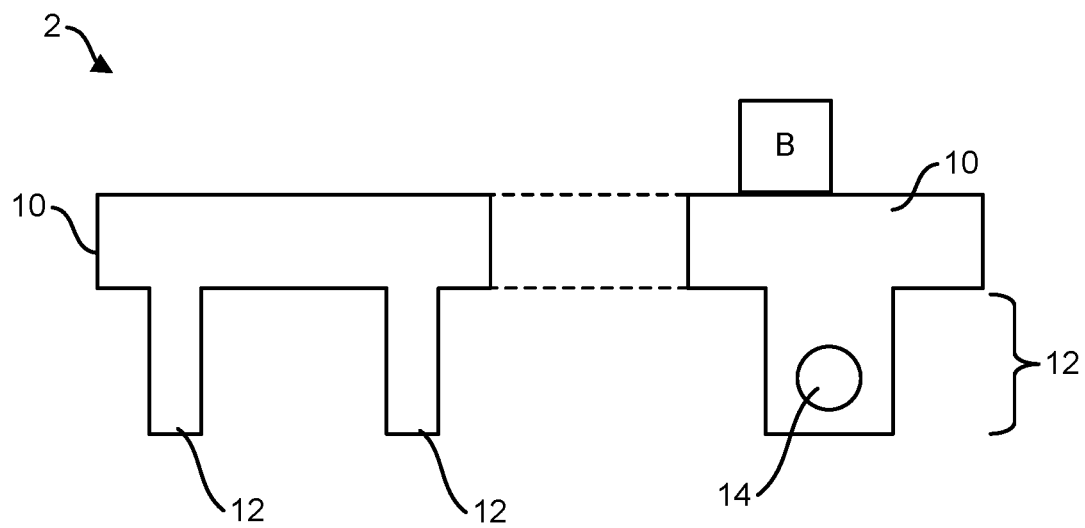
FIG. 3 is a side view of a head cap of a pedicle screw removal device according to an example embodiment.
Figure 4:
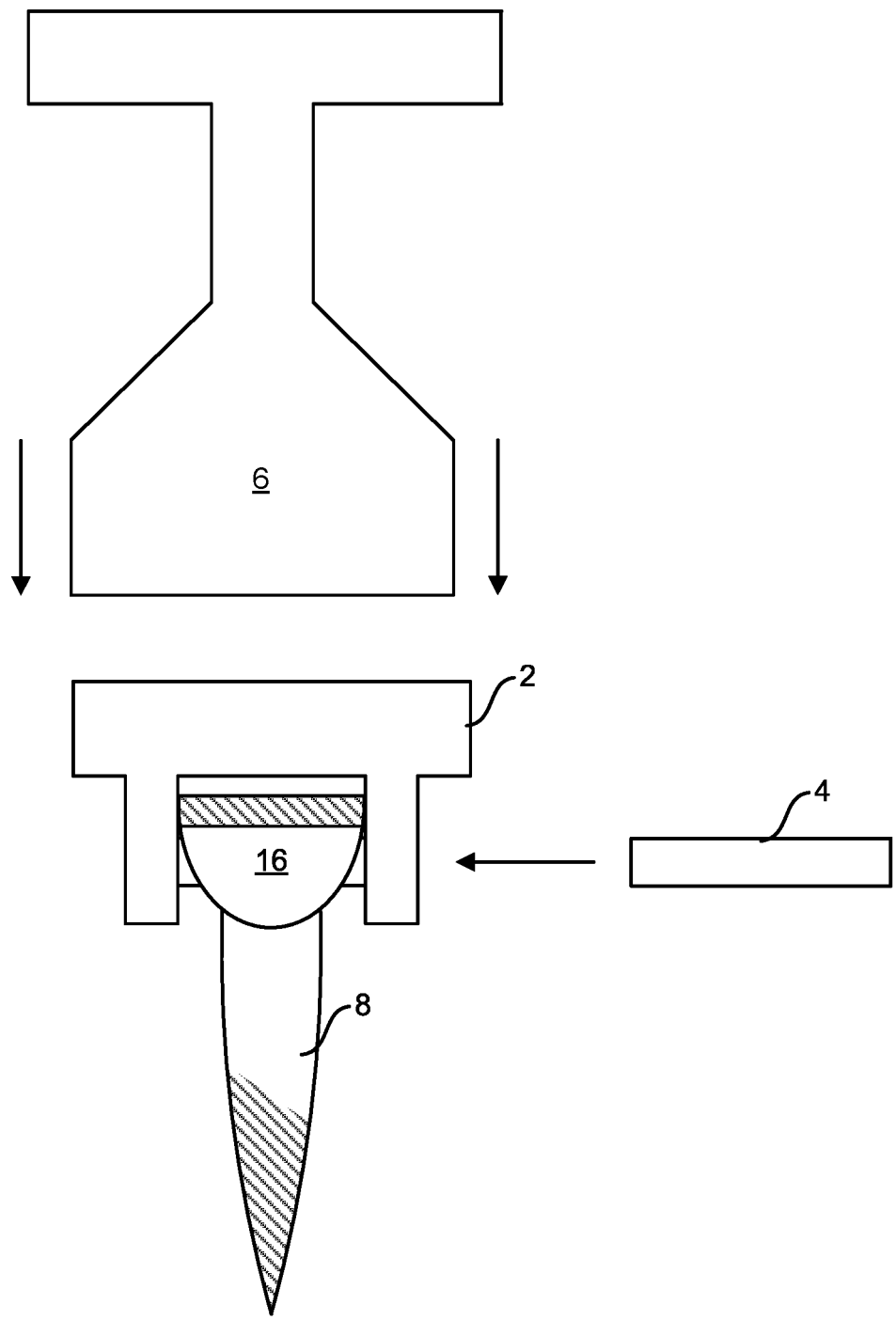
FIG. 4 illustrates a pedicle screw removal device according to an example embodiment secured to a pedicle screw and ready for removal.

Referring now to FIGS. 2 through 4, a head cap 2 according to an example embodiment is shown. In this example embodiment, the head cap 2 includes a body 10 and at least one arm 12 extending perpendicularly from the body 10. The at least one arm 12 may include a hole 14 through which the removal rod 4 may be inserted. The at least one arm 12 is configured to fit over the head 16 of the pedicle screw 8 (see FIG. 4). The hole 14 of the at least one arm 12 is configured to align with a groove or channel (not shown) in the head 16 of the pedicle screw 8. The removal rod 4 then passes through the hole 14 of the at least one arm 12 and the groove or channel in the head 16 of the pedicle screw 8 to secure the head cap 2 to the head 16 of the pedicle screw 8. Then, the removal handle 6 is fitted over the head cap 2, and the removal handle 6 may be rotated to remove the pedicle screw 8. Although the above description indicates that the removal rod 4 is inserted through hole 14 and the groove or channel in the head 16 of the pedicle screw 8 before the removal handle 6 is fitted over the head cap 2, this process may be reversed, in which the removal handle 6 may be fitted over the head cap 2 before the removal rod is inserted through hole 14 and the groove or channel in the head 16 of the pedicle screw 8.

In one example embodiment, body 10 of the head cap 2 may have a cross section shape that matches the cross section of the removal handle 6. For example, as shown in FIG. 2, the body 10 of head cap 2 may be octagonal to correspond to an octagonal removal handle 6.

According to an example embodiment, the pedicle screw 8 may include a locking cap 18, and multiple pedicle screws 8 may be linked together by a stabilizing rod 20 inserted through the groove or channel in the head 16 pedicle screw 8 (see FIG. 1). To remove the pedicle screw 8, the locking cap 18 must be removed from the pedicle screw 8 first. Then, the stabilizing rod 20 connecting multiple pedicle screws 8 may be removed to allow for insertion of the removal rod 4.

Figure 5:
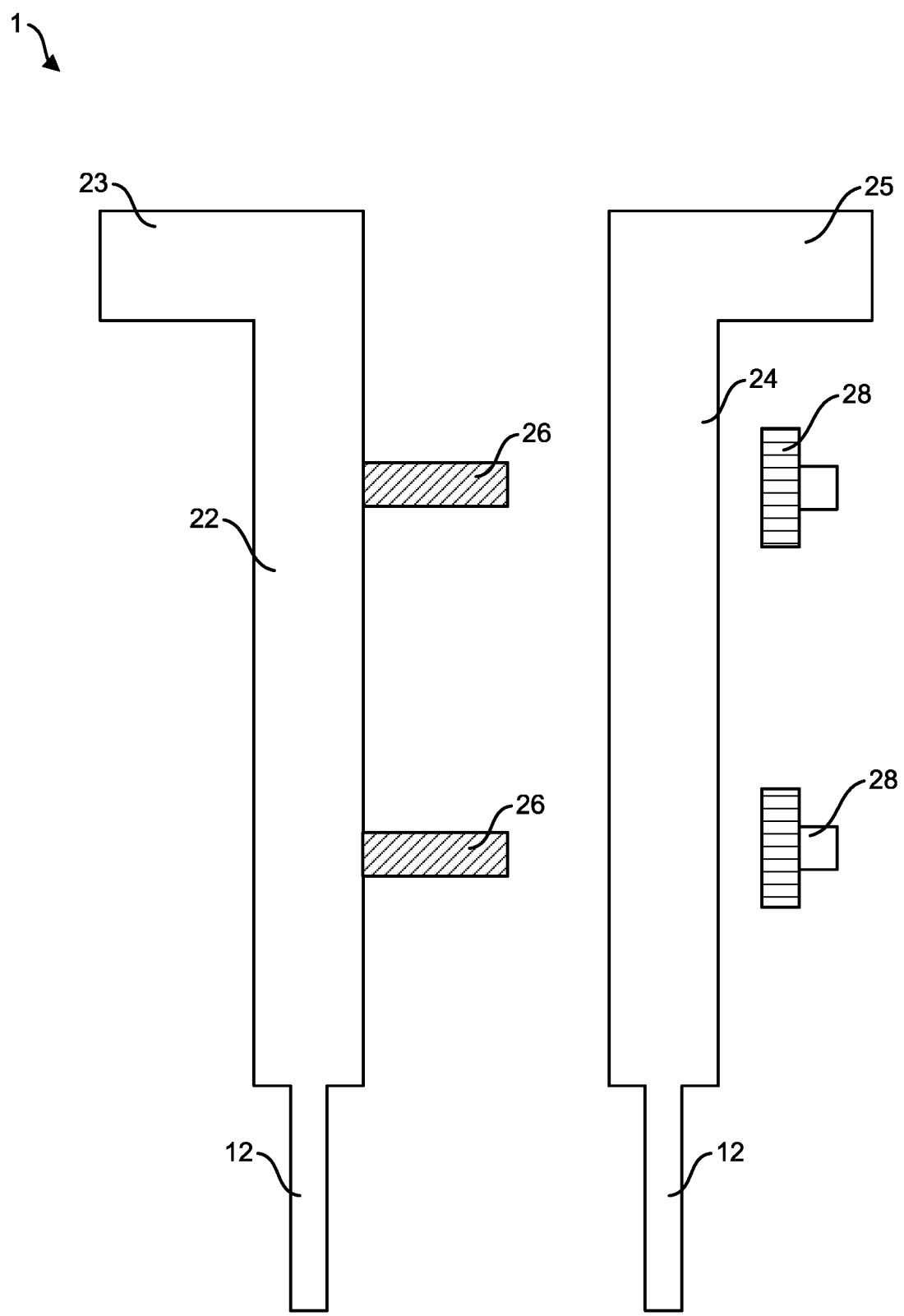
FIG. 5 illustrates a pedicle screw removal device according to another example embodiment.

Referring now to FIG. 5, a pedicle screw removal device according to another example embodiment is shown. This example embodiment of the pedicle screw removal device 1 includes two handles 22, 24 configured to be secured together by fastening means. In one example embodiment, the fastening means are at least one threaded bolt 26 on a first handle 22 and a corresponding at least one nut 28. The threaded bolts 26 on the first handle 22 pass through corresponding fastener holes 34 (see FIG. 6) on a second handle 24 where the nuts 28 are then fastened to the threaded bolts 26 to lock the first and second handles 22, 24 together. The first and second handles 22, 24 may respectively include first and second grip portions 23, 25 that may extend substantially perpendicularly from the first and second handles 22, 24 in opposing directions.

Figure 6:
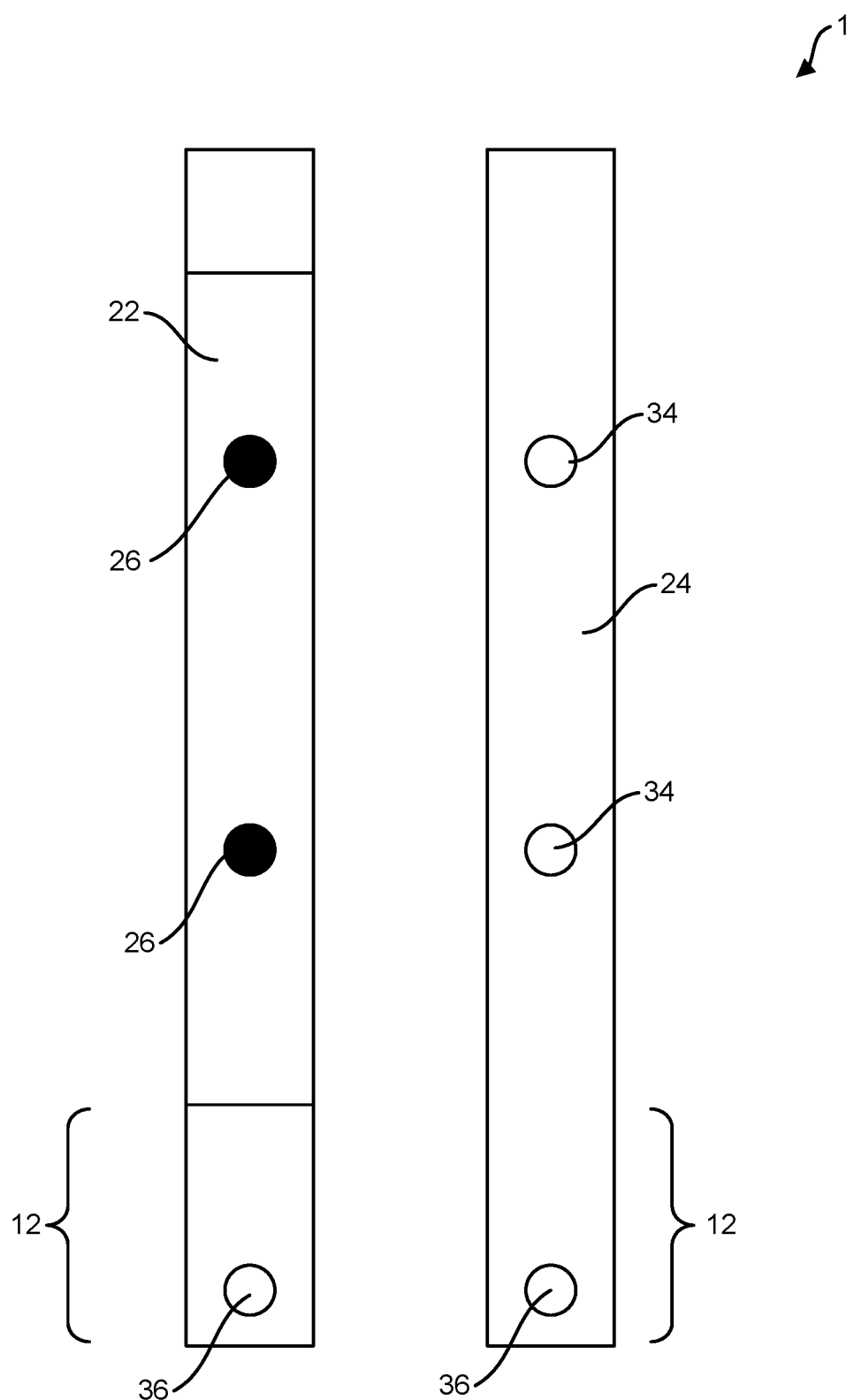
FIG. 6 shows a side view of the handles of a pedicle screw removal device according to an example embodiment.

Referring now to FIG. 6, a side view of the handles 22, 24 of the example embodiment of FIG. 5 are shown. The first handle 22 is shown with the threaded bolts 26 corresponding to fastener holes 34 on the second handle 24. Each of the handles 22, 24 has an arm 12 that is configured to secure on either side of the pedicle screw 8 (not shown). Each arm 12 has a rod hole 36 that is configured to receive the removal rod 4 when the removal rod 4 is inserted through the hole in the head 16 of the pedicle screw 8 (See FIG. 7).

Figure 7:
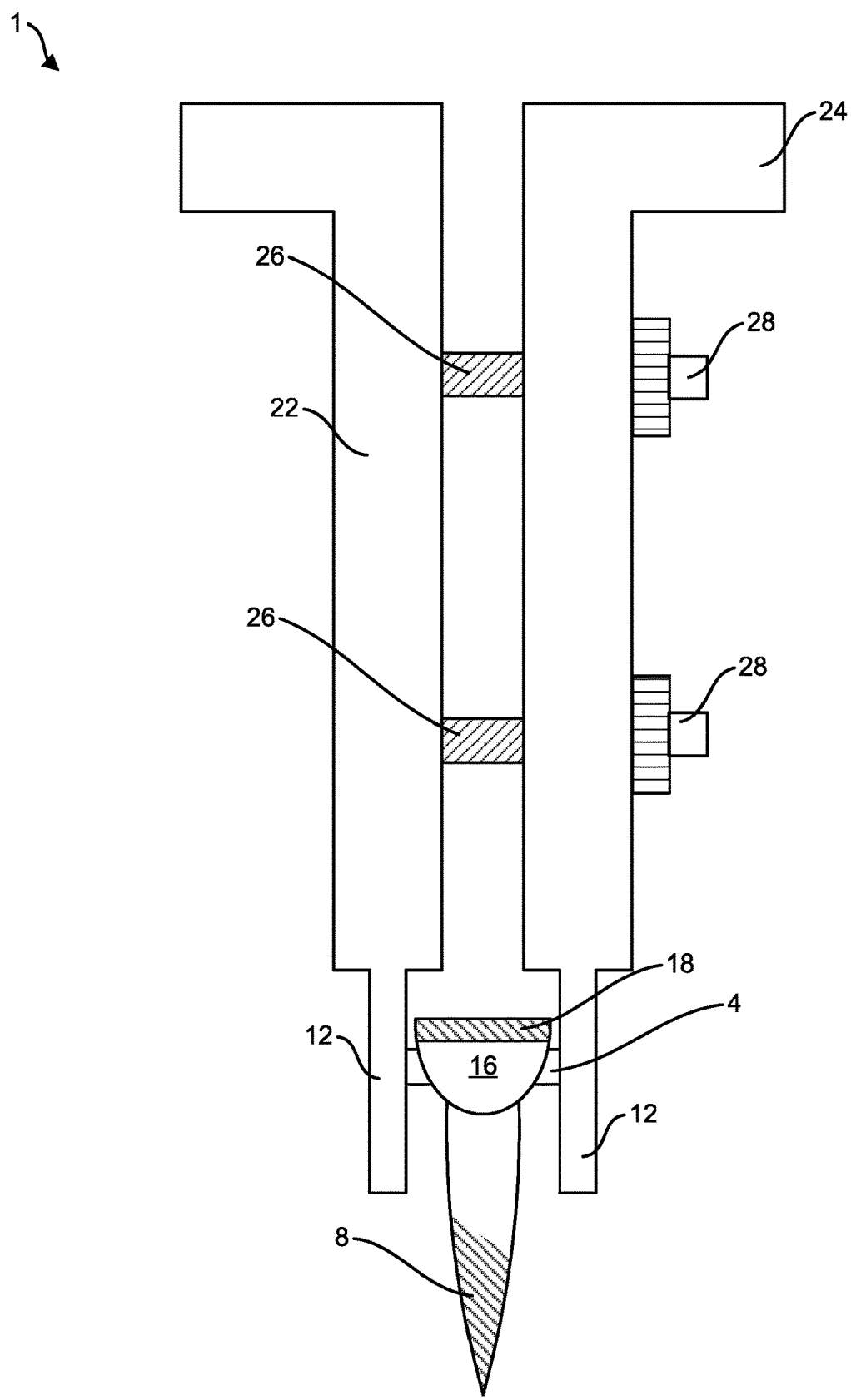
FIG. 7 illustrates a pedicle screw removal device according to an example embodiment secured to a pedicle screw.

Referring to FIG. 7, a pedicle screw removal device 1 is shown secured to a pedicle screw 8. To secure the pedicle screw removal device 1 to the pedicle screw 8, the locking cap 18 is removed from the pedicle screw 8 while the pedicle screw 8 is in place in the patient's spine. If multiple pedicle screws 8 are connected, the stabilizing rod 20 connecting the pedicle screws 8 is removed. The removal rod 4 may be placed into the groove or channel in the head 16 of the pedicle screw 8, and the locking cap 18 may be replaced. Handles 22, 24 may be placed on the screw head 16 so that the removal rod 4 projects through the holes 36 in the arms 12 of the handles 22, 24. The handles 22, 24 may be connected using the fastening means, for example by inserting threaded bolts 26 through fastener holes 34 and screwing corresponding nuts 28 on to threaded bolts 26 until tight. A surgeon may then rotate the handles 22, 24, using grip portions 23, 25 for example, to remove the pedicle screw 8.

Figure 8:
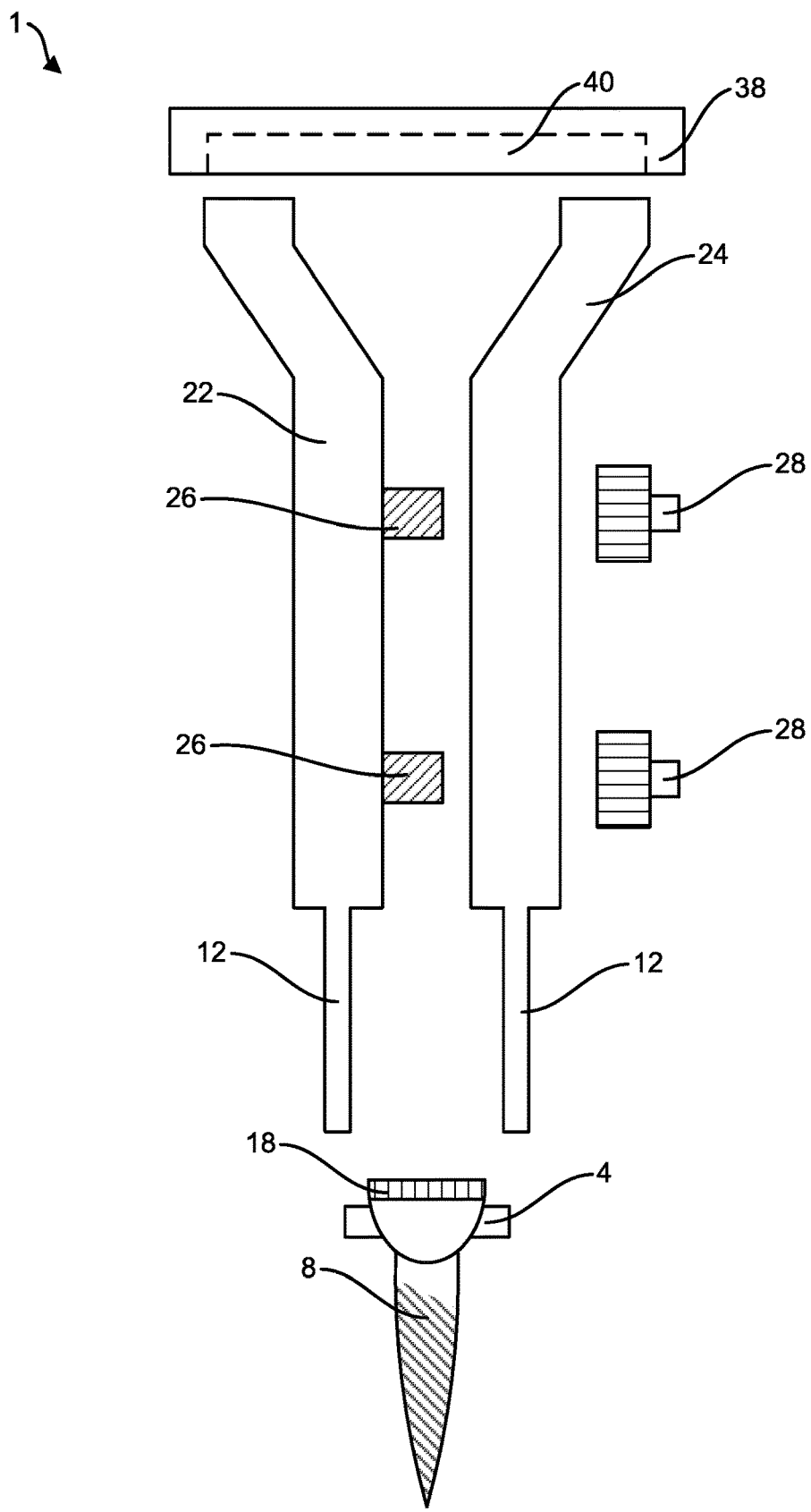
FIG. 8 illustrates another example embodiment of a pedicle screw removal device according to an example embodiment with a t-bar attachment.

Referring now to FIG. 8, a t-bar 38 may be included with some example embodiments of the pedicle screw removal device 1. The t-bar 38 has a cavity or opening 40 to receive and control the removal handles 22, 24. In example embodiments having a t-bar 38, the t-bar 38 may allow for increased control and a consistent rotation of both handles with respect to each other. The t-bar 38 may be placed over the top of the handles 22, 24 with the top of the handles 22, 24 fitting within the cavity 40. For example, the t-bar 38 may be sized and shaped to fit over grip portions 23, 25 shown in FIG. 5. Once the t-bar 38 is in place, a surgeon may rotate the t-bar 38 to remove the pedicle screw 8.

Figure 9:
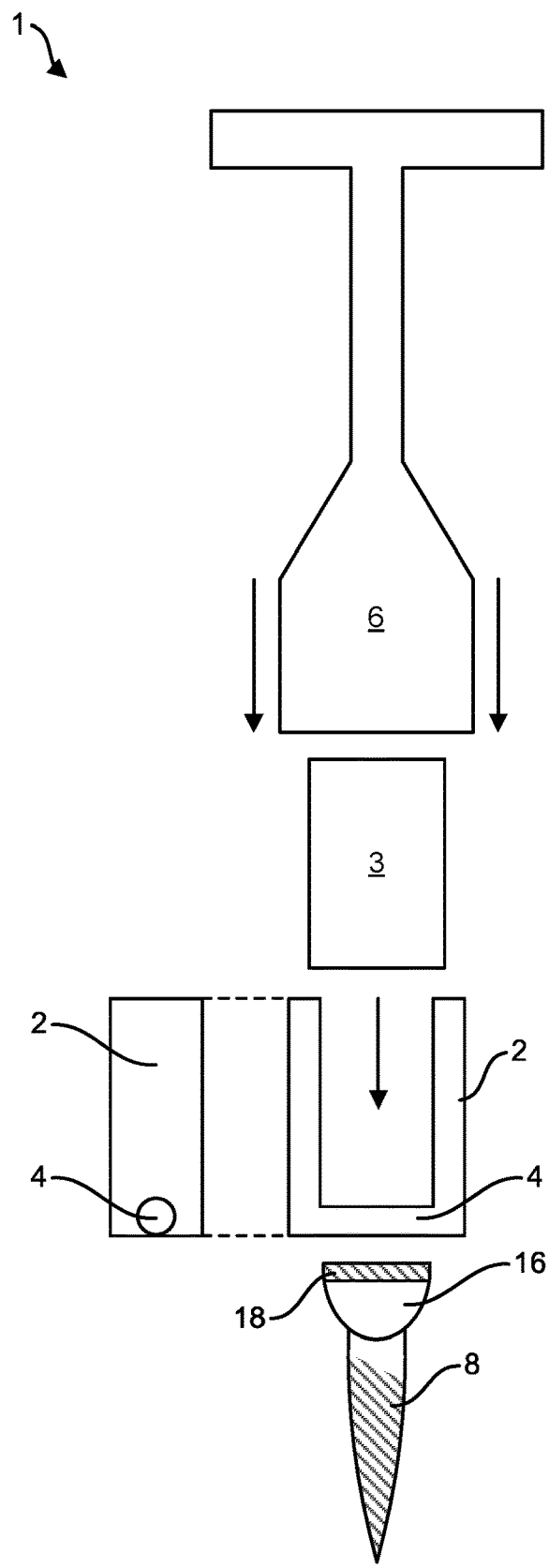
FIG. 9 illustrates another example embodiment of a pedicle screw removal device according to an example embodiment.

Referring to FIG. 9, another example embodiment of the pedicle screw removal device is shown. In some example embodiments, the pedicle screw removal device 1 may include a head cap 2 with an integral removal rod 4, a head cap insert 3, and a removal handle 6. To remove the pedicle screw 8, the locking cap 18 is removed from the pedicle screw 8 in place in the spine. If present, the connecting rod 20 connecting the pedicle screws 8 (not shown) is removed. The head cap 2 with integral removal rod 4 is placed such that the integral removal rod is located within the groove or channel in the head 16 of pedicle screw 8. More specifically, as shown in FIG. 9, the head cap 2 differs from the head caps 2 of the previously described example embodiments. The head cap 2 shown in the example embodiment of FIG. 9 includes two vertical components that are coupled to (or integrally formed with) the integral removal rod 4. The integral removal rod 4 is configured to fit into the groove or channel of the head 16 of pedicle screw 8, and the locking cap 18 may be replaced to secure the integral removal rod in place. The screw cap insert 3 may be inserted into the cavity created between the two vertical components, and above the horizontal component, of head cap 2. The screw cap insert 3 may provide stability to the head cap 2, allowing for additional torque to be applied to remove screw. The removal handle 6 is then placed over the head cap 2 and rotated to remove the pedicle screw 8.

Although the inventive concepts of the present disclosure have been described and illustrated with respect to exemplary embodiments thereof, it is not limited to the example embodiments disclosed herein and modifications may be made therein without departing from the scope of the inventive concepts.

What is claimed is:

1. A pedicle screw removal device comprising:
   a head cap configured to fit over a pedicle screw head;
   at least one hole in the head cap corresponding to a groove in the pedicle screw head;
   a removal rod configured to fit through the at least one hole in the head cap and the groove in the pedicle screw head to facilitate rotating the pedicle screw during removal; and
   a removal handle having a socket, the socket configured to engage the head cap and rotate the head cap to remove the pedicle screw in response to rotation of the removal handle.

2. The pedicle screw removal device of claim 1, wherein the head cap comprises:
   a body; and
   at least one arm extending substantially perpendicularly from the body;
   wherein said at least one hole comprises a hole in each of the at least one arms; and
   wherein the hole in each of the at least one arms is configured to receive the removal rod.

3. The pedicle screw removal device of claim 2, wherein the at least one arm is sized and shaped to engage the removal rod when the removal rod is disposed within said hole in each of the at least one arms, and rotate the pedicle screw in response to rotation of the removal handle.

4. The pedicle screw removal device of claim 1, wherein the head cap comprises:
   a body; and
   a first arm and a second arm extending substantially perpendicularly from the body;
   wherein said at least one hole in the head cap comprises a first hole in the first arm, and a second hole in the second arm; and
   wherein the first hole and the second hole are configured to receive the removal rod.

5. The pedicle screw removal device of claim 4, wherein the first and second arms are configured to fit on opposite sides of the pedicle screw head, and are configured to rotate the pedicle screw by rotating the removal rod.

6. A pedicle screw removal device comprising:
   a first handle having a first arm with a first hole;
   a second handle having a second arm with a second hole;
   a removal rod configured to pass through the first hole, through a head of a pedicle screw, and through the second hole; and
   one or more fastening mechanisms configured to couple the first handle to the second handle.

7. The pedicle screw removal device of claim 6, further comprising a t-bar having a cavity configured to fit over the first handle and the second handle.

8. The pedicle screw removal device of claim 6, further comprising a first grip portion coupled to the first handle, and a second grip portion coupled to the second handle;
   wherein the first grip portion extends substantially perpendicularly from the first handle, and the second grip portion extends substantially perpendicularly from the second handle.

9. The pedicle screw removal device of claim 8, wherein the first grip portion and the second grip portion extend in substantially opposite directions.

10. The pedicle screw removal device of claim 8, further comprising a t-bar having a cavity configured to fit over the first grip portion and the second grip portion.

11. The pedicle screw removal device of claim 6, wherein the one or more fastening mechanisms comprise one or more bolts coupled to the first handle and configured to extend through one or more respective holes in the second handle, and one or more nuts configured to be respectively coupled to said one or more bolts.

12. A pedicle screw removal device comprising:
    a head cap configured to engage a pedicle screw, said head cap including a first vertical portion and a second vertical portion separated from each other to form a cavity therebetween;
    an integral removal rod coupled to or integrally formed with the first and second vertical portions of the head cap, said integral removal rod configured to fit through a groove in a screw head of the pedicle screw; and
    a removal handle having a socket configured to engage the head cap and rotate the head cap to remove the pedicle screw in response to rotation of the removal handle.

13. The pedicle screw removal device of claim 12, further comprising a screw cap insert sized and shaped to fit within the cavity formed between the first and second vertical portions of the head cap.

14. The pedicle screw removal device of claim 12, wherein the integral removal rod is coupled to or integrally formed with end portions of the first and second vertical portions of the head cap.

* * * * *